US009103201B2

(12) United States Patent
Collins et al.

(10) Patent No.: US 9,103,201 B2
(45) Date of Patent: Aug. 11, 2015

(54) METHOD AND SYSTEM FOR CONFIGURING CRUDE OIL DISPLACEMENT SYSTEM

(75) Inventors: Ian Ralph Collins, Middlesex (GB); Stephanie Jane Houston, Farnborough (GB); Kevin John Webb, Worthing (GB)

(73) Assignee: BP EXPLORATION OPERATING COMPANY LIMITED, Middlesex (GB)

( * ) Notice: Subject to any disclaimer, the term of this patent is extended or adjusted under 35 U.S.C. 154(b) by 467 days.

(21) Appl. No.: 13/322,695

(22) PCT Filed: May 26, 2010

(86) PCT No.: PCT/GB2010/001038
§ 371 (c)(1),
(2), (4) Date: Feb. 15, 2012

(87) PCT Pub. No.: WO2010/139932
PCT Pub. Date: Dec. 9, 2010

(65) Prior Publication Data
US 2012/0143579 A1 Jun. 7, 2012

(30) Foreign Application Priority Data

Jun. 3, 2009 (EP) .................................... 09251481

(51) Int. Cl.
*E21B 43/20* (2006.01)
*E21B 43/16* (2006.01)
*C09K 8/58* (2006.01)

(52) U.S. Cl.
CPC . *E21B 43/16* (2013.01); *C09K 8/58* (2013.01); *E21B 43/20* (2013.01)

(58) Field of Classification Search
None
See application file for complete search history.

(56) References Cited

U.S. PATENT DOCUMENTS 3,768,560 A * 10/1973 Hill et al. ................... 166/270.1
3,885,628 A * 5/1975 Reed et al. ................. 166/252.1

(Continued)

OTHER PUBLICATIONS

L. C. Yong, "The Use of Dispersion Relationships to Model Adverse Mobility Ratio Miscible Displacements" 15 pgs., 1986.*

(Continued)

*Primary Examiner* — Kibrom K Gebresilassie
(74) *Attorney, Agent, or Firm* — Nixon & Vanderhye P.C.

(57) ABSTRACT

A computer-implemented method for determining one or more operating modes for a crude oil displacement system is provided. The crude oil displacement system is arranged to inject an aqueous displacement fluid into one or more reservoirs, each reservoir comprising a porous and permeable rock formation, wherein crude oil and formation water are contained within a pore space of the rock formation. The crude oil displacement system is for use in displacing crude oil from the pore space of the rock formation. The computer-implemented method comprises the steps of receiving measurement data associated with one or more chemical characteristics of the displacement fluid and one or more chemical characteristics of the rock formation, the crude oil and the formation water of the one or more reservoirs, and inputting the measurement data and data representing a predetermined volume of oil into a computer-implemented predictive model. The predictive model is operated so as to generate predicted data indicative of a predicted additional amount of oil, compared to the predetermined volume of oil, that will be displaced by configuring the crude oil displacement system so as to inject the displacement fluid having the chemical characteristics into the one or more reservoirs. On the basis of the predicted data, the one or more operating modes of the crude oil displacement system are determined. A further computer-implemented method employing the predictive model in which predicted data indicative of one or more predicted chemical characteristics of the displacement fluid are generated is also provided. Additionally, a system for configuring a crude oil displacement system is provided.

15 Claims, 8 Drawing Sheets

(56) References Cited

U.S. PATENT DOCUMENTS

| | | | |
|---|---|---|---|
| 3,915,233 A * | 10/1975 | Slusser | 166/307 |
| 4,163,475 A * | 8/1979 | Cha et al. | 166/250.15 |
| 4,240,504 A * | 12/1980 | Reed | 166/400 |
| 4,258,789 A * | 3/1981 | Hedges et al. | 166/252.3 |
| 4,262,746 A * | 4/1981 | Hammett | 166/400 |
| 4,279,305 A * | 7/1981 | Knapp et al. | 166/307 |
| 4,330,418 A * | 5/1982 | Glinsmann et al. | 507/259 |
| 4,448,698 A * | 5/1984 | Trushenski | 507/213 |
| 4,526,231 A * | 7/1985 | Radke | 166/270.1 |
| 4,969,130 A * | 11/1990 | Wason et al. | 367/73 |
| 5,301,751 A * | 4/1994 | Githens et al. | 166/283 |
| 5,388,646 A * | 2/1995 | Hensley | 166/271 |
| 6,668,922 B2 * | 12/2003 | Ziauddin et al. | 166/250.05 |
| 7,006,959 B1 * | 2/2006 | Huh et al. | 703/10 |
| 7,248,969 B2 * | 7/2007 | Patzek et al. | 702/13 |
| 7,324,929 B2 * | 1/2008 | Huh et al. | 703/10 |
| 7,680,640 B2 * | 3/2010 | Camilleri | 703/10 |
| 7,707,018 B2 * | 4/2010 | Shaw | 703/10 |
| 7,938,175 B2 * | 5/2011 | Skinner et al. | 166/57 |
| 7,987,907 B2 * | 8/2011 | Collins et al. | 166/252.3 |
| 8,141,632 B2 * | 3/2012 | Maksimenko et al. | 166/250.1 |
| 8,162,048 B2 * | 4/2012 | Termine et al. | 166/250.01 |
| 8,301,425 B2 * | 10/2012 | Dale et al. | 703/10 |
| 8,316,935 B1 * | 11/2012 | Termine et al. | 166/250.01 |
| 8,473,268 B2 * | 6/2013 | Benish et al. | 703/10 |
| 8,510,089 B2 * | 8/2013 | Rai et al. | 703/10 |
| 8,540,022 B1 * | 9/2013 | Termine et al. | 166/250.01 |
| 8,550,163 B2 * | 10/2013 | Al-Yousif et al. | 166/305.1 |
| 8,550,164 B2 * | 10/2013 | Al-Yousef et al. | 166/305.1 |
| 8,612,194 B2 * | 12/2013 | Horne et al. | 703/10 |
| 2002/0013687 A1 * | 1/2002 | Ortoleva | 703/10 |
| 2003/0008781 A1 * | 1/2003 | Gupta et al. | 507/240 |
| 2004/0112836 A1 * | 6/2004 | Manz et al. | 210/721 |
| 2006/0015310 A1 * | 1/2006 | Husen et al. | 703/10 |
| 2006/0020438 A1 * | 1/2006 | Huh et al. | 703/10 |
| 2006/0076956 A1 * | 4/2006 | Sjolie et al. | 324/324 |
| 2006/0122777 A1 * | 6/2006 | Patzek et al. | 702/6 |
| 2006/0224369 A1 | 10/2006 | Yang et al. | |
| 2007/0255500 A1 * | 11/2007 | Pita et al. | 702/11 |
| 2008/0015832 A1 * | 1/2008 | Tardy | 703/10 |
| 2008/0033656 A1 * | 2/2008 | Herwanger | 702/18 |
| 2008/0208476 A1 | 8/2008 | Karami et al. | |
| 2009/0248374 A1 * | 10/2009 | Huang et al. | 703/2 |
| 2009/0288881 A1 * | 11/2009 | Mullins et al. | 175/50 |
| 2010/0006283 A1 * | 1/2010 | Collins et al. | 166/261 |
| 2010/0059226 A1 * | 3/2010 | Termine et al. | 166/308.1 |
| 2011/0060572 A1 * | 3/2011 | Brown et al. | 703/10 |
| 2011/0175607 A1 * | 7/2011 | Fordham et al. | 324/303 |
| 2011/0184711 A1 * | 7/2011 | Altman et al. | 703/10 |
| 2012/0053920 A1 * | 3/2012 | Rai et al. | 703/10 |
| 2012/0310614 A1 * | 12/2012 | Beattie et al. | 703/10 |
| 2012/0330553 A1 * | 12/2012 | Mollaei et al. | 702/11 |
| 2013/0125630 A1 * | 5/2013 | Collins et al. | 73/64.56 |
| 2013/0338987 A1 * | 12/2013 | Cheng et al. | 703/10 |
| 2014/0345862 A1 * | 11/2014 | Jerauld et al. | 166/275 |

OTHER PUBLICATIONS

J. W. Gardner, f. M. Orr, P. D. Patel, "The Effect of Phase Behavior on $CO_2$-Flood Displacement Efficiency" pp. 2067-2081, 1981.*

Y. S. Wu, B. Bai, Efficient Simulation for low salinity Waterflooding in Porous and Fractured Reservoirs, pp. 1-13, 2009.*

G. W. Paul, "A simplified Predictive Model for Micellar Polymer Flooding" pp. 137-156, 1982.*

International Search Report for PCT/GB2010/001038 mailed Mar. 10, 2011.

Written Opinion of the International Searching Authority mailed Mar. 10, 2011.

Gary R Jerauld et al., "Modeling Low-Salinity Waterflooding", SPE International Oil and Gas Conference and Exhibition, No. SPE 102239, Sep. 24, 2008, pp. 1000-1012.

Lager A et al., "LoSal Enhanced Oil Recovery: Evidence of Enhanced Oil Recovery at the Reservoir Scale", SPE/DOE Symposium on Improved Oil Recovery, Apr. 20-23, 2008, pp. 1313-1324.

Yu-Shu Wu, Baojun Bai, "Efficient Simulation for Low-Salinity Waterflooding in Porous and Fractured Reservoirs", Society of Petroleum Engineers, No. 118830, Feb. 2, 2009-Feb. 4, 2009, pp. 1-13.

G.W. Paul et al., "A Simplified Predictive Model for Micellar-Polymer Flooding", Society of Petroleum Engineers, No. 10733, Mar. 24, 1982-Mar. 26, 1982, pp. 137-156.

Third Office Action dated Apr. 20, 2015, issued in corresponding Chinese Patent Application No. 201080034555.8, filed May 26, 2010, 5 pgs.

Third Office Action dated Apr. 20, 2015, issued in corresponding Chinese Patent Application No. 201080034555.8, filed May 26, 2010, 12 pgs., English Translation.

* cited by examiner

METHOD AND SYSTEM FOR CONFIGURING CRUDE OIL DISPLACEMENT SYSTEM

This application is the U.S. national phase of International Application No. PCT/GB2010/001038 filed 26 May 2010 which designated the U.S. and claims priority to EP 09251481.9 filed 3 Jun. 2009, the entire contents of each of which are hereby incorporated by reference.

FIELD OF THE INVENTION

The present invention relates to a computer-implemented method and a system for determining one or more operating modes for a crude oil displacement system. The method uses various chemical characteristics of an oil reservoir environment and of a crude oil displacement fluid in a predictive model to determine the one or more operating modes.

BACKGROUND OF THE INVENTION

It has long been known that only a portion of the total crude oil present in a reservoir can be recovered during a primary recovery process, this primary process resulting in oil being recovered under the natural energy of the reservoir. The reservoir typically takes the form of an oil-bearing subterranean rock formation having sufficient porosity and permeability to store and transmit fluids, and with which oil is associated, for example being held in pores or between grains of the rock formation. So-called secondary recovery techniques are used to force additional oil out of the reservoir, the simplest method of which is by direct replacement with another medium in the form of a displacement fluid, usually water or gas. Enhanced oil recovery (EOR) techniques can also be used. The purpose of such EOR techniques is not only to restore or maintain reservoir pressure, but also to improve oil displacement in the reservoir, thereby minimising the residual oil saturation of the reservoir, that is, the volume of oil present in the reservoir. Where the initial reservoir pressure is close to the bubble point of the crude oil, secondary or enhanced oil recovery techniques may be used early in the life of a field, for example, primary recovery may not occur.

"Waterflooding" is one of the most successful and extensively used secondary recovery methods. Water is injected, under pressure, into reservoir rock formations via injection wells. The injected water acts to help maintain reservoir pressure, and sweeps the displaced oil ahead of it through the rock towards production wells from which the oil is recovered. The water used in waterflooding is generally saline water from a natural source such as seawater or may be a produced water (i.e. water that is separated from the crude oil at a production facility).

It is also known that the use of a lower salinity injection water during water-flooding can increase the amount of oil recovered compared to the use of a higher salinity water. It is also known that reducing the multivalent cation content of a lower salinity injection water can have an impact on the oil recovery. However, lower salinity waters, such as fresh water, are often not available at a well site, for example at offshore oilfields, and have to be made by reducing the total dissolved salt (TDS) concentration and/or the concentration of multivalent cations of a source water using desalination techniques such as reverse osmosis or forward osmosis. Source waters that are known to be treated in this manner include seawater, brackish water, produced water and aquifer water.

"Lower" or "low" salinity water is hereinafter intended to define water having a total dissolved solids content (TDS) in the range of 200 to 15,000 ppmv, preferably, 500 to 12,000 ppmv. Where the formation rock contains swelling clays, in particular, smectite clays, a relatively high TDS for the low salinity water is required in order to stabilise the clays, thereby avoiding the risk of formation damage. Thus, where the formation rock contains an amount of swelling clays sufficient to result in formation damage, the low salinity water preferably has a total dissolved solids content (TDS) in the range of 8,000 to 15,000 ppmv, in particular, 8,000 to 12,000 ppmv. Where the formation comprises amounts of swelling clays that do not result in formation damage, the TDS of the source water is typically in the range of 200 to 8,000 ppmv, preferably 500 to 8,000 ppmv, for example, 1,000 to 5,000 ppmv. As discussed above, the low salinity water also has a low concentration of multivalent cations of typically 40 ppmv or less, preferably less than 35 ppmv, more preferably, less than 30 ppmv, for example, less than 25 ppmv. However, it is preferred that the low salinity water contains at least some multivalent cations. Thus, a multivalent cation content of the low salinity water in the range of 5 to 40 ppmv, preferably, 10 to 40 ppmv is acceptable.

The water present in the pore space of a rock, hereinafter referred to as "formation water", can vary in composition. Where a displacement fluid is injected without performing primary recovery or immediately after primary recovery, the formation water will typically comprise connate water, and where a displacement fluid is injected after a previous waterflood, the formation water will typically comprise a mixture of connate water and a previously injected water such as sea water or produced water.

The factors that control the interactions between crude oil, the rock formation, the injection or displacement fluid and the formation water, and their effect on wettability and oil recovery, involve complex and sometimes competing mechanisms. It has also been found that a factor in improving oil recovery during a low salinity waterflood is the use of an injection water of a lower multivalent cation content or concentration than that of the formation water. Thus, greater oil recovery is achieved when the ratio of the total multivalent cation content of the aqueous low salinity displacement fluid to the total multivalent cation content of the formation water is less than 1, for example, less than 0.9. Generally, the lower the ratio of the total multivalent cation content of the aqueous low salinity displacement fluid to the total multivalent cation content of the formation water (hereinafter "multivalent cation ratio for the low salinity aqueous displacement fluid"), the greater the amount of oil that is recovered from a particular formation. Thus, the multivalent cation ratio for the low salinity aqueous displacement fluid is preferably less than 0.8, more preferably, less than 0.6, yet more preferably, less than 0.5, and especially less than 0.4 or less than 0.25. The multivalent cation ratio for the low salinity aqueous displacement fluid may be at least 0.001, preferably, at least 0.01, most preferably, at least 0.05, in particular at least 0.1. Preferred ranges for the multivalent cation ratio for the low salinity aqueous displacement fluid are 0.01 to 0.9, 0.05 to 0.8, but especially 0.05 to 0.6 or 0.1 to 0.5.

It is also possible to inject a slug of low salinity water of controlled oil reservoir pore volume, PV. The term "pore volume" is used herein to mean the swept volume between an injection well and a production well and may be readily determined by methods known to the person skilled in the art. Generally, the pore volume (PV) of the slug of low salinity water is at least 0.2 PV, as a slug of lower pore volume tends to dissipate in the formation and may not result in appreciable incremental oil production. It has also been found that where the pore volume of the softened injection water is at least 0.3, preferably, at least 0.4, the slug tends to maintain its integrity within the formation (does not disperse within the formation) and therefore continues to sweep displaced oil towards a production well. Thus, the incremental oil recovery for a particular formation approaches a maximum value with a slug of at least 0.3 PV, preferably at least 0.4 PV, with little additional incremental oil recovery with higher pore volume slugs.

Although, it is possible to continue to inject the low salinity water into a formation, typically, the pore volume of the slug of low salinity water is minimized since there may be limited injection capacity for the low salinity water owing to the need to dispose of produced water. Also, there may be limited availability of a naturally occurring low salinity water or where the low salinity water is produced using desalination techniques, the capacity of the desalination equipment may be limited owing to operation costs and weight considerations (where the desalination plant is located on a platform or floating production, storage and off-loading (FPSO) facility). Thus, the pore volume of the low salinity water is preferably less than 1, more preferably less than 0.9 PV, most preferably, less than 0.7 PV, in particular, less than 0.6 PV, for example, less than 0.5 PV. Typically, the slug of low salinity water has a pore volume in the range of 0.2 to 0.9, preferably 0.3 to 0.6, and especially 0.3 to 0.45. After injection of a pore volume of the low salinity water that achieves close to the maximum incremental oil recovery (preferably, a slug of softened injection water having a pore volume of less than 1), a drive (or post-flush) water of higher multivalent cation content and/or higher TDS, usually both, may be injected into the formation (for example, seawater or a high salinity produced water) thereby ensuring that the slug of softened injection water (and hence the released oil) is swept through the formation to the production well. In addition, the injection of the post-flush water may be required to maintain the pressure in the reservoir. After injection of a pore volume of the low salinity water that achieves close to the maximum incremental oil recovery, the low salinity water may be injected into a different hydrocarbon-bearing formation of the oil reservoir or into a hydrocarbon-bearing formation of a different oil reservoir.

It has also been found that enhanced oil recovery using low salinity water is dependent upon the nature of the formation that contains the crude oil and formation water. Thus, it is preferred that the formation comprises a sandstone rock and at least one mineral that has a negative zeta potential under the formation conditions.

Currently, laboratory core flood testing (where a sample of rock is removed from a reservoir, before oil production begins or during primary recovery, and is then placed under the reservoir conditions for testing in the laboratory) or single well chemical tracer testing (where a fluid labelled with appropriate chemical tracers is injected into a formation via an injection well and produced back from the same well) are applied in order to determine the residual oil saturation of the formation following a low salinity waterflood, and based on the results, a decision can be made as to whether or not a waterflood using lower salinity water is worthwhile. These tests are time consuming and the results are often not available during the planning stage of an oil field development. Accordingly, in the absence of tests results showing enhanced oil recovery using a low salinity waterflood, there may be a reluctance to include desalination equipment in the design for the production facility.

SUMMARY OF THE INVENTION

In accordance with one aspect of the present invention, there is provided a computer-implemented method for determining one or more operating modes for a crude oil displacement system, the crude oil displacement system being arranged to inject an aqueous displacement fluid into one or more reservoirs, each reservoir comprising a porous and permeable rock formation, wherein crude oil and formation water are contained within a pore space of the rock formation, said crude oil displacement system being for use in displacing crude oil from the pore space of the rock formation,
the method comprising the steps of:
receiving measurement data associated with one or more chemical characteristics of the displacement fluid and one or more chemical characteristics of the rock formation, the crude oil and the formation water of the one or more reservoirs;
inputting said measurement data and data representing a predetermined volume of oil into a computer-implemented predictive model;
operating the predictive model so as to generate predicted data indicative of a predicted additional amount of oil, compared with the predetermined volume of oil, that will be displaced by configuring the crude oil displacement system so as to inject said displacement fluid having said chemical characteristics into the one or more reservoirs; and
determining, on the basis of the predicted data, said one or more operating modes of the crude oil displacement system.

In accordance with the above aspect, the invention further provides a system for configuring a crude oil displacement system, the crude oil displacement system being arranged to inject an aqueous displacement fluid into one or more reservoirs, each reservoir comprising a porous and permeable rock formation, wherein crude oil and formation water are contained within a pore space of the rock formation, said crude oil displacement system being for use in displacing crude oil from the pore space of the rock formation, the system comprising:
data receiving means arranged to receive measurement data based on one or more chemical characteristics of the displacement fluid and one or more chemical characteristics of the rock formation, the crude oil and the formation water of the one or more reservoirs;
prediction means for generating, based on the measurement data and data representing a predetermined volume of oil, predicted data indicative of a predicted additional amount of oil, compared with the predetermined volume of oil, that will be displaced by configuring the crude oil displacement system so as to inject said displacement fluid having said measured chemical characteristics into the one or more reservoirs; and
operating mode determining means arranged to determine, on the basis of the predicted data, one or more operating modes of the crude oil displacement system.

The use of the predictive model or "displacement" model minimises or avoids altogether the testing steps referred to above; further it provides a prediction of the amount of additional or incremental oil, compared with a predetermined volume of oil, that could potentially be produced by waterflooding the formation with a low salinity water (as defined above) as opposed to, for example, a high salinity water, based on chemical characteristics of the reservoir environment, including those of the rock formation, the crude oil and the formation water, and on chemical characteristics of the aqueous displacement fluid (i.e. the low salinity water).

In accordance with a further aspect of the present invention, there is provided a computer-implemented method for determining one or more operating modes for a crude oil displacement system, the crude oil displacement system being arranged to inject an aqueous displacement fluid into one or more reservoirs, each reservoir comprising a porous and permeable rock formation, wherein crude oil and formation water are contained within a pore space of the rock formation, said crude oil displacement system being for use in displacing crude oil from the pore space of the rock formation, the method comprising the steps of:
receiving measurement data associated with one or more chemical characteristics of each of the rock formation, the crude oil and the formation water of the one or more reservoirs;
inputting said measurement data, data representing a predetermined volume of oil and a predetermined threshold value of a required additional amount of displaced oil compared with the predetermined volume of oil, into a computer-implemented predictive model;
operating the predictive model so as to generate predicted data indicative of one or more predicted chemical characteristics of the displacement fluid; and
determining, on the basis of the predicted data, said one or more operating modes of the crude oil displacement system.

In accordance with the further aspect, the invention further provides a system for configuring a crude oil displacement system, the crude oil displacement system being arranged to inject an aqueous displacement fluid into one or more reservoirs, each reservoir comprising a porous and permeable rock formation, wherein crude oil and formation water are contained within a pore space of the rock formation, said crude oil displacement system being for use in displacing crude oil from the pore space of the rock formation, the system comprising:

data receiving means arranged to receive measurement data based on one or more chemical characteristics of each of the rock formation, the crude oil and the formation water of the one or more reservoirs;
prediction means for generating, based on the measurement data, data representing a predetermined volume of oil and a predetermined threshold value of a required additional amount of displaced oil compared with the predetermined volume of oil, predicted data indicative of one or more predicted chemical characteristics of the displacement fluid; and
operating mode determining means arranged to determine, on the basis of the predicted data, one or more operating modes of the crude oil displacement system.

By including a value indicative of a required amount of incremental displaced oil in the input characteristics, chemical characteristics of the displacement fluid to be injected to displace this amount of incremental oil, such as those relating to the salinity of the displacement fluid, can be predicted.

Based on predicted data generated by the model, an operating mode of the crude oil displacement system can be determined. For example, it may be determined that water of a relatively low salinity could be used in a waterflood, or it may be determined that it is only worthwhile performing a waterflood using seawater or a high salinity produced water.

Further features and advantages of the invention will become apparent from the following description of preferred embodiments of the invention, given by way of example only, which is made with reference to the accompanying drawings.

BRIEF DESCRIPTION OF THE DRAWINGS

FIG. 4b shows the steps carried out in a method according to an embodiment of the invention with respect to the reservoirs of FIG. 4a;

FIG. 5b shows the steps carried out in a method according to an embodiment of the invention with respect to the reservoir sections of FIG. 5a.

DETAILED DESCRIPTION OF THE INVENTION

Figure 1:
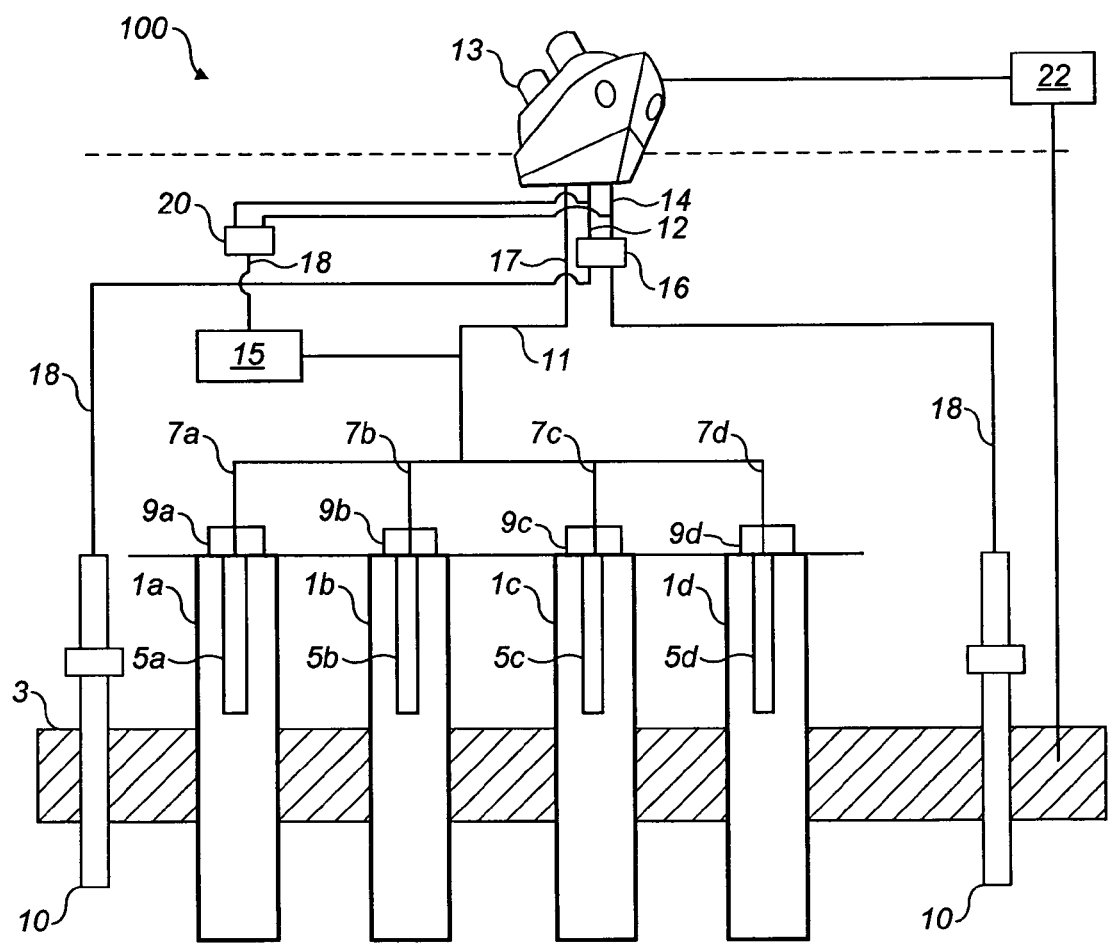
FIG. 1 is a schematic diagram showing a crude oil displacement system which is configurable in conjunction with embodiments of the invention.

FIG. 1 is a schematic block diagram showing a simplified representation of a crude oil recovery system 100 for an offshore oil field. In this Figure, a plurality of production wells 1a to 1d is used to drain at least one rock formation making up an oil reservoir 3. Each production well 1a, 1b, 1c, 1d has a production tubing 5a, 5b, 5c, 5d arranged therein and is provided with a wellhead 9a, 9b, 9c, 9d, respectively. Accordingly, the production tubing of each production well serves to transport fluids, including crude oil, produced from the reservoir 3 to the wellhead. From the wellhead 9a, 9b, 9c, 9d the produced fluids pass into a flow line 7a, 7b, 7c, 7d which connects with a main flow line 11 which transfers the produced fluids to a production facility 13 located on a platform or floating production, storage and offloading installation (FPSO) via riser 17. Moreover, an additional oil reservoir (either single or multiple oil reservoirs, each reservoir having a plurality of production wells), such as generally shown by means of part 15, may be joined to the main flow line 11. The crude oil recovery system 100 also includes at least one, preferably, a plurality of injection wells 10 for injecting an aqueous displacement fluid into the rock formation of oil reservoir 3 (similarly, the additional oil reservoir(s) of part 15 are each provided with at least one injection well, preferably, a plurality of injection wells). A first main injection line 12 for a pressurised high salinity water (such as seawater or a produced water that is separated from the crude oil at the production facility 13) and a second main injection line 14 for a pressurised low salinity water (produced using desalination equipment located on the platform or FPSO) extend from the production facility 13 to a subsea manifold 16 for reservoir 3. Dedicated injection line(s) 18 extend from the subsea manifold 16 to the injection well(s) for reservoir 3. Moreover, the first and second main injection lines 12, 14 may lead to one or more additional manifold(s) 20 for each of the additional oil reservoir(s) of part 15. A controller (not shown) is provided for operating valves of the manifold(s) 16, 20 such that the dedicated injection lines(s) 18 can be switched between receiving pressurised low salinity water and pressurised high salinity water.

Each reservoir 3 comprises at least one rock formation, which is porous and permeable, such as sandstone, and which comprises at least one mineral that has a negative zeta potential (that is, a negative surface electric charge) under reservoir conditions. This mineral may be a clay, for example a kaolinite or smectite type clay.

A crude oil displacement system of the recovery system 100 generally comprises equipment arranged to inject a displacement fluid, preferably an aqueous displacement fluid such as sea water, into the one or more crude oil-bearing reservoirs 3. For example, the displacement system typically comprises one or more displacement fluid injection wells 10 (as shown in FIG. 1), one or more injection lines for the displacement fluid, and a controller arranged to control the fluid injection. The displacement system may also comprise equipment associated with the treatment of the displacement fluid in preparation for injection, such as desalination equipment.

The aqueous displacement fluid is injected by injection equipment of the crude oil displacement system into the injection well(s) 10 thereof. The aqueous displacement fluid then passes through the rock formation in which crude oil and formation water are present, resulting in displacement of the crude oil from a pore space of the rock formation. The oil can then be swept through the formation to a production well 1a to 1d spaced from the injection well 10, from which it is recovered.

Figure 2:
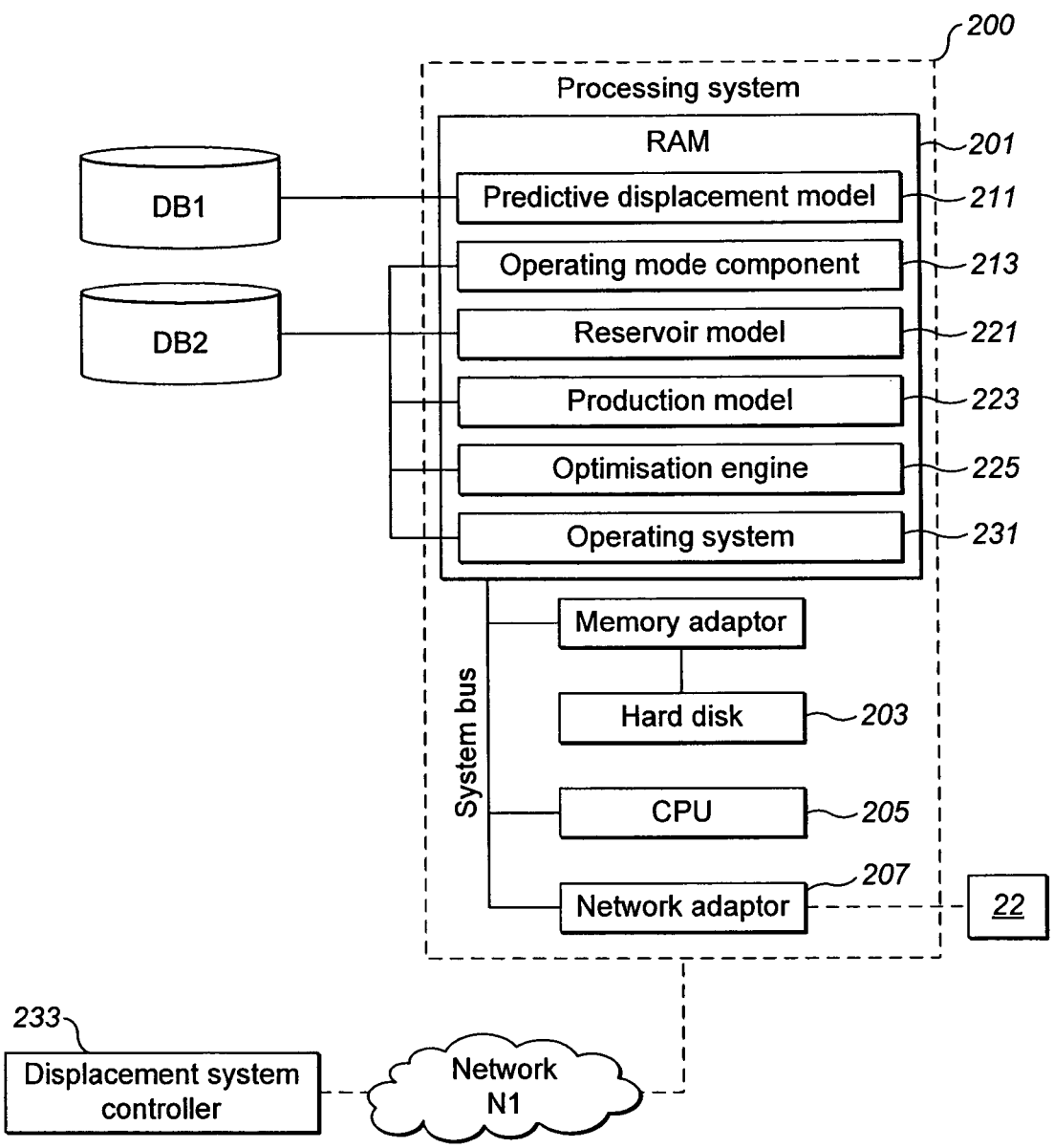
FIG. 2 shows a system for determining one or more operating modes for a crude oil displacement system, according to an embodiment of the present invention.

In order to determine optimum settings of the various components of the oil recovery system 100, the system is simulated by means of one or more models, as shown in FIG. 2, each dedicated to a specific part of the recovery system 100. A reservoir model 221, which, as known in the art, is a conceptual 3-dimensional construction of a reservoir that is constructed from incomplete data with much of the inter-well space estimated from data obtained from nearby wells or from seismic data, may be employed. In conjunction with this, a reservoir simulation, that is, a computer model that predicts the flow of fluids through porous media (and is therefore based on the reservoir model) may be employed. A predictive model 211 according to embodiments of the invention, as described further below, can predict the amount of incremental oil displaced from the reservoir rock. Using the reservoir model 221, the reservoir simulation can use information such as the volume and shape of the reservoir 3 (including the arrangement of overlying rock formations and the locations of any faults or fractures in the rock formations), the porosity of the oil-bearing rock formations, the permeability of the oil-bearing rock formation(s) in different directions (including the relative permeabilities to oil and water), the initial oil saturation of the oil-bearing rock formation(s), the location of production well(s) 1a to 1d and injection well(s) 10, the predicted sweep (the volume of the reservoir swept by a displacement fluid that is injected down the injection well(s) 10), in combination with the results of the predictive model 211, to provide an indication as to how much of the predicted displaced oil can be recovered at the productions well(s) 1a to 1d. Additionally, there can be one model associated with the oil recovery system 100 (which inclusively couples the reservoir 3 with the components of the displacement system and with components of the production facility 13). Alternatively, there can be one model associated with the displacement system and one model 223 associated with the production facility 13. The additional model(s) enable calculation of flow rates and pressures at any point in the oil recovery system based on predefined operating characteristics of the components making up the recovery system 100 and specified operating conditions.

In one arrangement, referring to FIG. 2, the predictive model 211 (also referred to as a displacement model) of the invention and optionally the reservoir model 221 associated with the reservoir 3 and the production model 223 associated with the production facility 13, are executed by a processing system 200, for example a control system on a platform, which can comprise conventional operating system and storage components such as a system bus connecting a central processing unit (CPU) 205, a hard disk 203, a random access memory (RAM) 201, I/O and network adaptors 207 facilitating connection to user input/output devices and interconnection with other devices on a network N1. The Random Access Memory (RAM) 201 contains operating system software 231 which controls, in a known manner, low-level operation of the processing system 200. The server RAM 201 contains the models 211, 221, 223 during execution thereof. Each model is configurable with measurement and/or predetermined data stored in a database or other storage component which is operatively coupled or connected to the processing system 200; in the system of FIG. 2, storage component DB1 stores all such data relating to the predictive model 211 and is accessible thereby, while storage component DB2 stores all other data for use by the other components of the system 200. An optimisation engine 225 may be provided as described below with reference to FIG. 6.

Measurement data received by receiving means of the system 200 are based on measured chemical characteristics of the oil reservoir 3 environment and of the aqueous displacement fluid, as explained further below. The measurement data may comprise specific measured chemical values as directly measured by suitably positioned measurement equipment 22, or ratios of values of chemical characteristics, or may comprise values derived from a number of separate chemical characteristic measurements, according to known techniques. Therefore, the raw measured chemical characteristics may, if necessary or preferred, be manipulated by appropriate software, executed by the CPU 205 of the system 200, in order to generate measurement data that are suitable for inputting into the predictive model 211. Such manipulation may simply comprise a measurement unit conversion or the creation of a required ratio of measured values.

The predictive model can be populated with data that correlates known incremental oil recovery following a waterflood with the chemical characteristics of the oil reservoir environment and of the aqueous displacement fluid.

The additional or incremental amount of oil that is predicted by the predictive model 211 is an amount, in terms of, for example, a percentage, fraction or volume, of oil that will be displaced or recovered compared with a predetermined volume of oil, which is input into the predictive model 211. The predetermined volume of oil may comprise a "base" oil displacement (or recovery) volume, which is calculated by running a simulation of a "base waterflood" using the reservoir model 221. This base value reflects the oil that could be either recovered or displaced (both calculations are possible by the reservoir model) based on the physical parameters of the aqueous displacement fluid (such as injection pressure, volume of the displacement fluid, and injection rate) and on physical parameters of the particular reservoir(s) (such as reservoir pressure, porosity and permeability of the formation rock). Thus, the calculated value from the simulation of the "base waterflood" is not dependent on the chemical displacement referred to above and therefore the chemical characteristics of the aqueous displacement fluid (such as salinity and/or multivalent cation content) and the chemical characteristics of the reservoir rock are irrelevant for the purposes of this calculation. Typically, this additional or incremental amount of oil is expressed as a percentage or fraction of the predetermined base value. Alternatively, the additional or incremental volume of oil may be calculated using the predictive model based on a predetermined volume of oil that represents the original volume of oil calculated or estimated to be in place in the reservoir before any displacement or recovery of oil (before primary recovery), or immediately before the proposed injection of the displacement fluid (for example, after primary recovery or after secondary recovery with a different displacement fluid). Alternatively, the predetermined volume of oil can be an amount of oil that has previously been recovered from the reservoir(s) in question; if required, the reservoir model 221 can be used to calculate or estimate the volume of oil displaced based on that recovered (as it is unlikely that 100% of all oil displaced will be recovered during a waterflood), to provide a more accurate comparison with the predicted additional amount of oil displaced.

The system 200 is preferably operatively connected to a controller 233 of the crude oil displacement system, for example via the network N1. The controller 233 of the displacement system is automatically configured with the one or more operating modes determined by the system 200, the controller 233 being arranged to apply the one or more operating modes.

Figure 3:
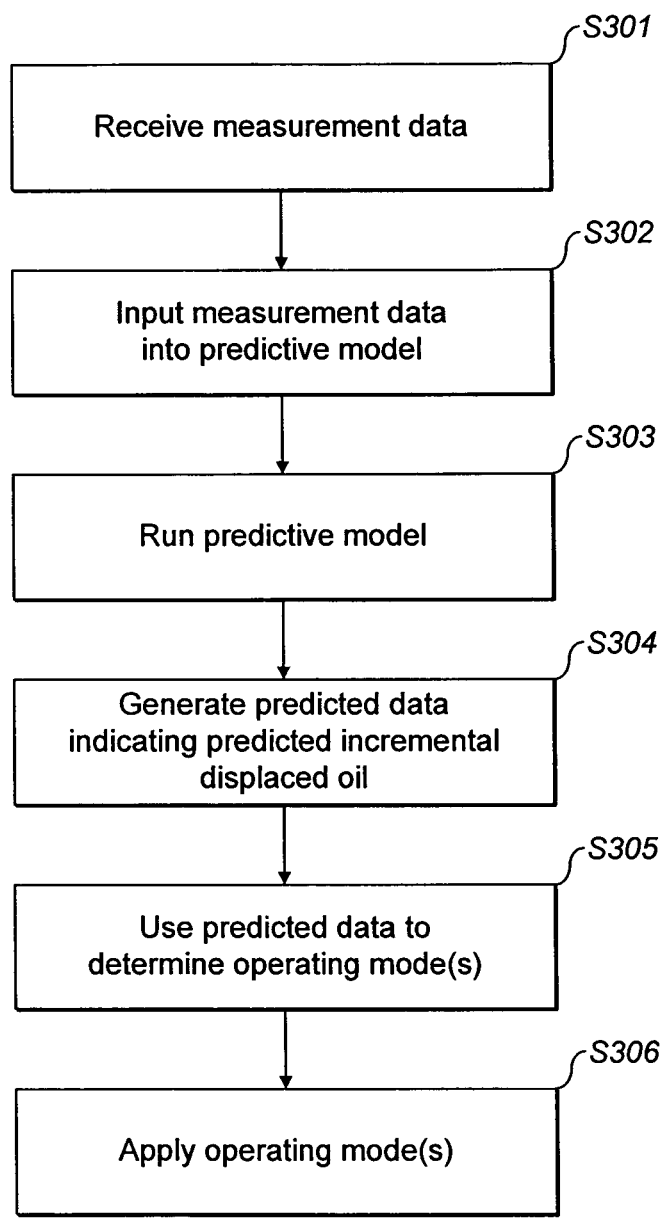
FIG. 3 shows the steps carried out in a method for determining one or more operating modes for a crude oil displacement system, according to a first embodiment of the invention.

Referring to FIG. 3, the steps involved in a first embodiment of a computer-implemented method for determining one or more operating modes for the crude oil displacement system are shown.

In step S301, measurement data associated with measurements of one or more chemical characteristics of the aqueous fluid proposed for injection and one or more chemical characteristics of the rock formation, the crude oil and the formation water of the reservoir 3 in question are received. The chemical characteristics of the rock formation can be determined from samples of the rock formation such as rock cuttings, or a side wall core or by direct measurement of the rock present in the reservoir 3. Samples of produced sand can also be used to determine chemical characteristics of the rock formation. The chemical characteristics of the proposed aqueous displacement fluid can be determined by direct measurement of the aqueous displacement fluid. The chemical characteristics of the crude oil and the formation water can be determined by direct measurement of the fluids present in the reservoir 3 or by measurement of samples of the fluids taken from the reservoir. For example, the chemical characteristics for the rock formation, crude oil and formation water can be determined upon an initial assessment or appraisal of a reservoir 3 when developing a new oil field. As discussed below, these measurements of one or more chemical characteristics of the aqueous displacement fluid, and one or more chemical characteristics of the rock formation, the crude oil and the formation water of the reservoir are determined using standard chemical analytical techniques that are well known to the person skilled in the art.

At step S302, the measurement data are input into a computer-implemented predictive model 211, which includes statistical analysis software, and is described further below. Data representing the predetermined volume of oil, as described above, is also input into the model. The predictive model 211 is then run in step S303, and generates, at step S304, predicted data indicative of a predicted amount of incremental oil that will be displaced by configuring the crude oil displacement system so as to inject the aqueous displacement fluid having the measured chemical characteristics into the reservoir 3. The predicted amount of incremental oil displaced may be provided by the predictive model 211 as a value representing a percentage value of the predetermined volume of oil.

Optionally, by using the results of the predictive model 211 and running the reservoir model 221 to simulate recovery of the displaced oil at the production wells, the reservoir model predicts a residual oil saturation that will be achieved by waterflooding the reservoir 3 using the proposed aqueous displacement fluid and compares this residual oil saturation with an oil saturation of the reservoir that would have been achieved using a higher salinity water as determined by the reservoir model, thereby providing a prediction of the incremental oil recovery. The predictive model 211 and the reservoir model 221 can also be used to compare the predicted incremental oil recoveries that will be achieved using aqueous displacement fluids having different measured chemical characteristics, thereby identifying the optimal chemical composition for the aqueous displacement fluid for the reservoir environment. A minimum acceptable value of the predicted incremental oil displaced or recovered (for example, <1% incremental oil recovery or <0.5% incremental oil recovery), below which desalination of the injection water is not deemed worthwhile, may be applied. Such a minimum acceptable value is dependent upon factors such as the volume of the reservoir, the resources available and/or economic considerations.

At step S305, the predicted data are used to determine one or more operating modes of the crude oil displacement system. The operating mode can represent an instruction or suggested setting for the displacement system, which can subsequently be applied to the displacement system. The determination preferably includes the step of comparing, in accordance with a predetermined set of rules as described further below, the predicted data and a predetermined threshold value of incremental oil stored in database DB1. For example, the determination may be based on a predetermined threshold value of a required amount of incremental displaced oil, or based on a predetermined threshold value, in terms of an amount or a percentage, by which the displaced oil increases compared to an amount of previously recovered oil from the one or more reservoirs 3.

Once the predictive model has run and predicted data are generated, software executed by the CPU 205 of the system 200 determines, on the basis of the predicted data, the one or more operating modes of the crude oil displacement system. The predictive model 211 itself may be configured to determine the operating mode(s) upon generation of the predicted data, or a separate software component 213 may be provided. Measurement and/or predetermined data, such as the predetermined threshold value of a required amount of incremental oil displaced, can be stored and accessed from the databases DB1 and DB2 as necessary.

For example, the operating mode can comprise an instruction to go ahead with the injection of a low salinity aqueous displacement fluid or not, this determination being based on a predetermined threshold amount of predicted incremental displaced oil for which it is assessed to be worthwhile performing the injection of the displacement fluid. Alternatively or additionally, the operating mode can comprise one or more specific configuration settings for the displacement system, such as a specific volume of displacement fluid to be injected. The operating mode determination can be made based on a predetermined value by which a required amount of displaced oil must increase compared to an amount of previously recovered oil from the one or more reservoirs 3.

The predictive model 211, or the separate software component 213 for determining the operating mode, are configured to use a predetermined set of rules in conjunction with input data such as the relevant specified thresholds and/or predetermined values and the predicted data, in order to determine the operating mode. These rules are stored in and accessible from the database DB1 and DB2 as necessary.

The computer-implemented method can further include an optional step, S306, of applying or inputting the determined operating mode into a controller of the displacement system.

The predictive model may comprise a statistical software package such as that provided by SAS® JMP®. The relevant data is compiled, for example into a Microsoft® Office Excel spreadsheet, which is opened using the SAS® JMP® package. A series of crossplots of specific chemical characteristic data against a value for the benefit gained (for example, the incremental oil percentage) are produced using the "Analyze, Fit Y by X" function, for example, a crossplot of incremental oil percentage against oil API, or incremental oil percentage against the calcium concentration of the injected water. The crossplots are then used to build a high level picture of which chemical characteristics are most relevant (i.e. produce the best correlations). A software tool which applies principle component analysis to the data can be used to determine which chemical characteristics to input into a "Fit Model" function. Alternatively, a choice of chemical characteristics can be made manually. The incremental oil percentage data is then added to the "Y variables" and other chosen chemical characteristics are added to "construct model effects". The model results are then exported to a program such as Microsoft® Office Excel and a test fit can be applied with existing data in order to verify the model.

As described above with reference to FIG. 3, in order for the predictive model 211 to generate data indicative of a predicted amount of incremental displaced oil that will be achieved by configuring the crude oil displacement system so as to inject the displacement fluid having the measured chemical characteristics into the reservoir 3, measurement data associated with certain chemical characteristics of the aqueous displacement fluid, rock formation, formation water and crude oil should be input into the model 211. These chemical characteristics include: the whole rock clay content of the reservoir rock, which can be determined by X-ray diffraction (XRD), scanning electron microscopy (SEM) or infrared scintillation point counting; the mineral content of the clay fraction of the rock, in particular, clays of the smectite type (such as montmorillonite), pyrophyllite type, kaolinite type, illite type and glauconite type, which can be determined by X-ray diffraction (XRD) or scanning electron microscopy (SEM); the American Petroleum Institute (API) gravity (relative density) of the oil; the total acid number (TAN value, a measurement of acidity) of the oil; the content of asphaltene and resin components of the oil; the total dissolved solids content (TDS) of the formation water, the concentration of multivalent cations of the formation water; the concentration of multivalent cations of the proposed aqueous displacement fluid; and the TDS content (indicating the salinity) of the proposed aqueous displacement fluid.

Other preferred or more specific chemical characteristics which may be measured to provide the measurement data input into the model are: a whole rock XRD analysis of the rock formation, including all mineral types in reservoir rock (including clays, and transition metal compounds, such as oxides and carbonates, for example, iron oxide, siderite, and plagioclase feldspars); the zeta potential of the rock; the base number of the oil; a total oil SARA analysis (SARA stands for saturates, aromatics, resins and asphaltenes and is a full evaluation of how much of each type of oil component is present in a sample); the oil viscosity at reservoir pressure and temperature; the viscosity of the stock tank crude oil (the oil that has been separated at the production facility) at standard conditions (for example, the viscosity measurement may be made at 20° C., 25° C. and 30° C.); the magnesium, calcium, barium and/or iron concentration of the formation water; the pH of the formation water; the magnesium, calcium, barium and/or iron concentration of the aqueous displacement fluid; and the pH of the displacement fluid.

Additional parameters can be taken into account as required in order to configure the predictive model 211. Some additional parameters that may be considered are: pour point temperature of the oil (° C.); cloud point temperature of the oil (° C.); density of the oil at 15° C. (g/ml) or at some other standard temperature; boiling point distribution of the oil (wt %); boiling point distribution of the oil (° C.); total nitrogen content of the oil (ppm wt); basic nitrogen content of the oil (ppm wt); surface tension of the oil (mN/m); oil/salt water interfacial tension (mN/m); and oil/fresh water interfacial tension (mN/m).

Data relating to the nature of the tests used by the measurement equipment 22 in deriving the measurement data, and any data relating to tests used in validating the predictive model 211, can also be taken into account. This data, together with the measurement data itself, is stored in the database DB1 and/or DB2 and read into the predictive model 211 as required.

The predictive model 211 may be populated with data obtained using existing coreflood data and single well chemical tracer (SWCT) test data which are used to validate the model. Data relating to field trials can also be used in validating the model. Thus, the predictive model 211 will be populated with various chemical characteristics of various aqueous displacement fluids used in the core flood tests, SWCT tests or field trials, and with various chemical characteristics of the rock formation, the crude oil, and the formation water for various reservoirs for which the core flood tests, SWCT tests or field trials were undertaken, while the reservoir model 221 may be populated with known residual oil saturation data for various reservoirs following a water flood (based on coreflood tests or SWCT tests or field trials) with various aqueous displacement fluids having various chemical characteristic values, and can therefore determine estimates of corresponding oil displacement values. The system software then determines correlations between the chemical characteristics and the displaced oil and uses these correlations to predict displacement of oil from the pore space of the formation rock of a modelled reservoir 3 and, if run in conjunction with the reservoir model 221, the incremental oil recovery for the modelled reservoir 3.

The computer-implemented method is advantageous in a number of applications, some of which are described in detail below.

The use of the predictive model 211 minimises or avoids altogether the testing steps and/or waterflooding using a high salinity water such as seawater or a produced water before using a lower salinity aqueous displacement fluid, and provides a prediction of the incremental oil that could potentially be recovered following a waterflood with a low salinity water, based on the measured chemical characteristics. Based on the predicted data, which preferably indicate a value for the incremental oil displacement as a percentage of the volume of oil indicated by the data input into the predictive model 211, the system 200 can determine an optimum or suggested operating mode, and typically takes additional data into account when doing so. This additional data may include data regarding the necessary volume of displacement fluid that can be provided and injected into the reservoir 3 via the fluid injection well 10, and any technical constraints or resource requirements that may affect the provision of the displacement fluid, such as the requirement to use desalination equipment to produce the required volume of displacement fluid. In general, a low salinity aqueous displacement fluid is either passed continuously into the formation or a slug of the low salinity aqueous displacement fluid of controlled pore volume (PV) is passed into the formation. As discussed above, the "pore volume" is known by a person skilled in the art to mean the swept volume between an injection well 10 and a production well 1a, 1b, 1c, 1d. The pore volume may be readily determined by known methods, including software modelling techniques.

The predictive model 211 can be run with measurement data relating to displacement fluids of different salinity, and is therefore an efficient method for predicting whether it is advantageous to perform a secondary recovery process using an aqueous displacement fluid of a lower salinity and/or multivalent cation content than that of a higher salinity water such as seawater or a produced water.

Advantageously, any core flood laboratory testing and/or single well chemical tracer tests can be minimised or avoided altogether, saving time, effort and resources in determining the optimal course of action. Where core flood laboratory testing and/or single well chemical tracer tests are carried out for a reservoir, the results of these tests can be input into the predictive model thereby further validating or refining the model.

As the required chemical characteristics can be measured upon initial appraisal of a reservoir 3, a determination as to whether or not desalination equipment should be included in the production facility of an offshore oilfield, can be made based on the operating mode determined at the initial engineering stage, again saving time, effort and resources by avoiding any need to retro-fit such equipment on an ad-hoc basis once oil recovery has begun.

The method also provides greater certainty than current "trial and error" approaches to waterflooding.

Figure 4A:
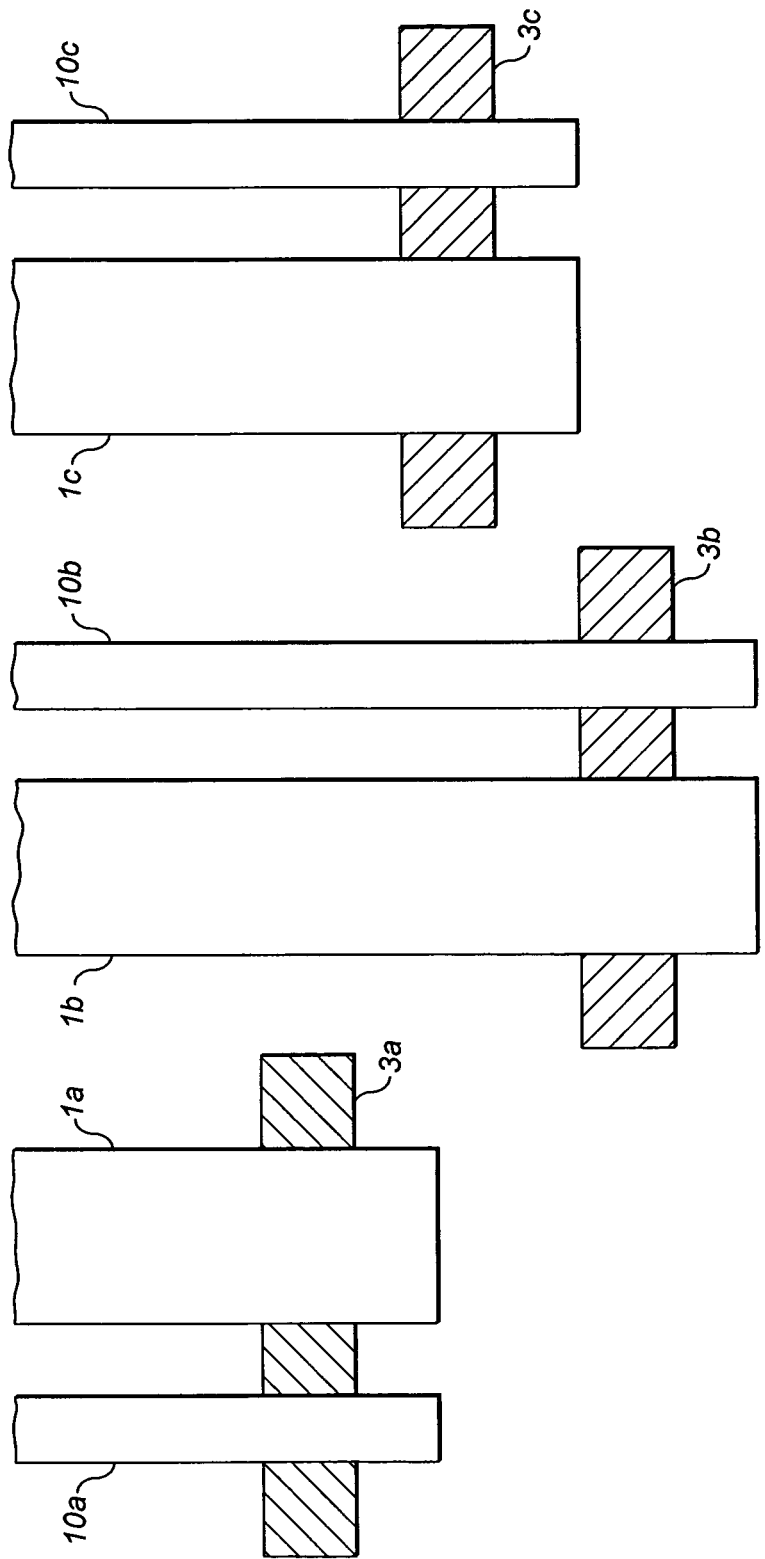
FIG. 4a shows three reservoirs which may be injected with a displacement fluid according to one or more operating modes determined by an embodiment of the method and system of the present invention.
Figure 4B:
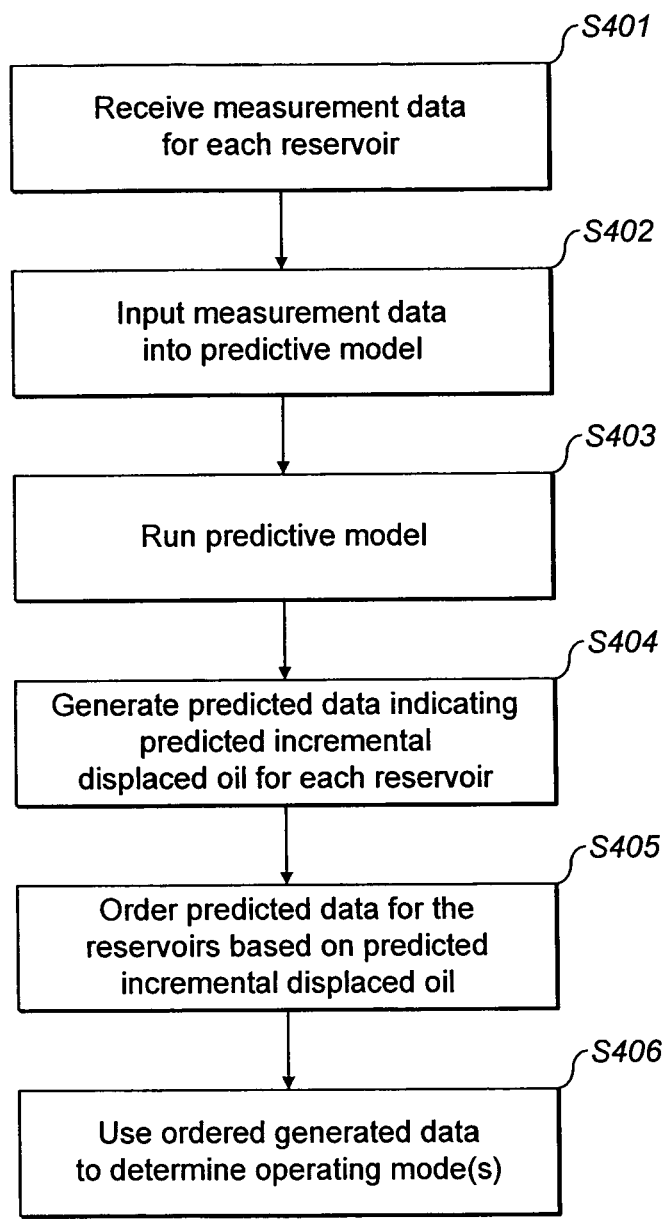

The measurement data, and hence the predicted data generated by the predictive model 211, may include data relating to measurements of the chemical characteristics of one or more reservoirs 3, and therefore the predictive model 211 may be run to determine an operating mode for the displacement system which affects a plurality of reservoirs. For example, the operating point can comprise an instruction to inject the displacement fluid into a plurality of reservoirs 3a, 3b and 3c, as shown in FIG. 4a. Each of the reservoirs 3a to 3c is operatively connected to the oil displacement system having the configuration described in FIG. 1. Preferably, each reservoir will have a plurality of production wells and a plurality of injection wells. FIG. 4a illustrates a displacement system where reservoirs 3a, 3b and 3c each have at least one production well 1a to 1c, and at least one injection well 10a to 10c. Referring to FIG. 4b, steps S401 to S403 correspond generally to those of the method of FIG. 3, with measurement data associated with measured chemical characteristics being received for each of the reservoirs 3a to 3c in step S401. The predictive model is run with the measurement data as input, and the predicted data of the predictive model 211 associated with each of the reservoirs 3a to 3c are determined (step S404) and can be ordered (step S405) based on the predicted amount of incremental oil that will be displaced. The one or more operating points are determined (step S406) based on the ordered results.

This application of the computer-implemented method and system is advantageous where a limited supply of naturally occurring aqueous displacement fluid having an optimal or required salinity and/or optimal or required multivalent cation content is present, and/or any desalination equipment produces a limited supply of aqueous displacement fluid having an optimal or required salinity and/or an optimal or required multivalent cation content. The application of the computer-implemented method and system is also advantageous where the volume of the optimal displacement fluid that can be injected into one or more reservoirs is limited owing the need to dispose of produced water by injecting the produced water into the reservoir(s).

For example, in running the predictive model 211 with the measurement data of each of reservoirs 3a to 3c of FIG. 4a, where a limited volume of a low salinity water for use as displacement fluid is available ("low salinity water" is as defined above), the predicted data generated by the model 211 may indicate that reservoir 3a is predicted to yield an incremental oil recovery of 8% based on the original oil in place in the reservoir, while values of 12% and 4% are predicted for reservoirs 3b and 3c, respectively. The system software can be configured to order or rank the reservoirs in priority order based on these results, and the predictive model 211 or other system software (such as the reservoir model 221) used in determining the operating mode can take into account factors such as the initial oil saturation of each reservoir (initial oil in place), an available volume of the low salinity water for use as displacement fluid and the slug volume required to displace the incremental oil for each reservoir 3a to 3c. It will be appreciated that a lower percentage value of a higher amount of initial oil in place may result in more oil being displaced and/or recovered than a higher percentage of a lower initial amount of oil in place, and this may influence the rankings of the reservoirs. If it is assumed that each of reservoirs 3a to 3c have similar initial oil saturations, the operating mode may, on this basis, comprise an instruction to inject the low salinity water into reservoir 3b, or to inject the low salinity water into reservoir 3b followed by reservoir 3a, followed by reservoir 3c or if sufficient low salinity water is available, to inject the low salinity water into both reservoir 3a and 3b followed by reservoir 3c. Optionally, a threshold value of incremental oil to be displaced may be applied, below which the reservoir should not be flooded for reasons of efficiency; in the example above, where a threshold of incremental displaced oil of 5% is applied, the operating mode comprises an instruction to flood reservoirs 3b and 3a, but not reservoir 3c. The predictive system may present this instruction to a user or may be operatively coupled to a controller of the crude oil displacement system such that the controller is automatically configured with the operating mode(s), for example to immediately carry out the injection(s).

Where there is a requirement to re-inject produced water, the predictive model can also be used to predict the incremental oil displacement for each reservoir if the produced water is used as displacement fluid or a blend of produced water and low salinity water is used as displacement fluid. The system software can be configured to order or rank the reservoirs in priority order for the re-injection of produced water based on these results taking into account the volume of produced water that it is desired to re-inject. The system software can also be configured to provide a modified ranking of the reservoirs that takes into account the incremental oil displacement that would be achieved using the low salinity water as displacement fluid, and the incremental oil displacement that would be achieved using the produced water as displacement fluid (or a blend of the low salinity water and produced water), taking into account the available volume of the low salinity injection water and the volume of produced water that it is desired to re-inject.

Figure 5A:
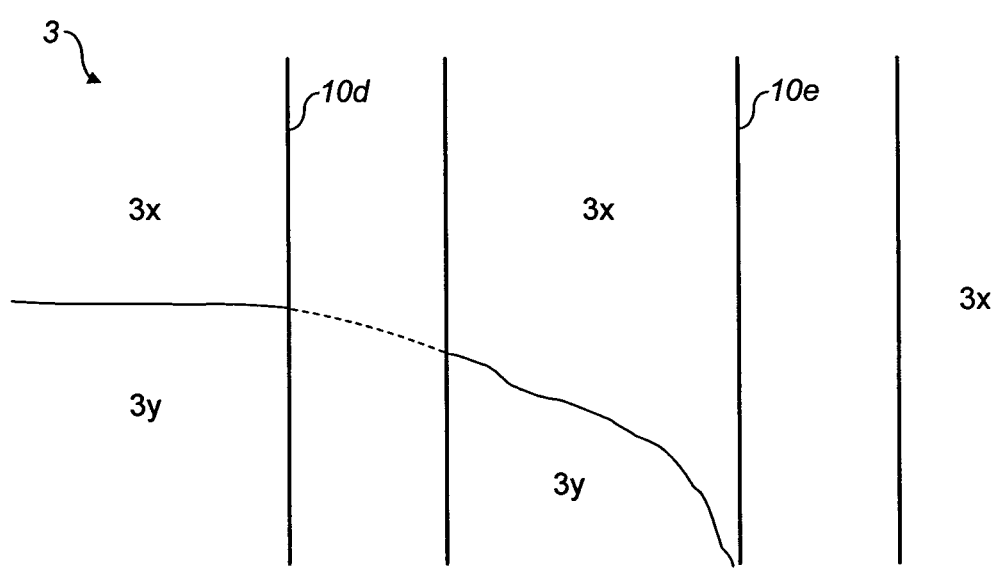
FIG. 5a shows two sections of a reservoir, which may be injected with a displacement fluid according to one or more operating modes determined by an embodiment of the method and system of the present invention, each section having different chemical characteristics.

Referring to FIG. 5a, a further example of an application of the computer-implemented method and system will be described. It is known that the chemical properties or characteristics of rock formations, oil and formation water can vary spatially within a single reservoir (both in a vertical and a transverse direction). Thus, where the reservoir comprises two or more overlying oil-bearing rock formations (hereinafter referred to as overlying sections of a reservoir), these overlying sections may have different chemical characteristics (owing to differences in the chemical characteristics of the rock formations, or to differences in the chemical characteristics of the crude oil or of the formation water contained within the pores of the rock formations). The overlying sections of the reservoir may have different initial oil saturations (also referred to as initial oil in place). Also, chemical properties or characteristics of a rock formation, oil and formation water can vary across a layer of a reservoir such that different chemical properties or characteristics can be measured at different locations. The initial oil saturation may also vary across a layer of a reservoir. Considering a reservoir having a plurality of injection wells at different positions in the reservoir, the computer-implemented method can determine an operating mode comprising an indication of which of the wells the displacement fluid, having measured chemical characteristics on the basis of which measurement data has been input into the predictive model 211, should be injected into in order to maximise the incremental oil displaced and hence potentially recovered. Thus, the predictive model may include measurements of the chemical characteristics of the reservoir rock, oil and formation water in different overlying layers of a reservoir as well as including measurements of such chemical characteristics at different locations within a layer of the reservoir.

FIG. 5a shows a reservoir 3 having two different overlying sections, referred to as sections 3x and 3y, section 3x being an upper reservoir section and section 3y being a lower reservoir section. It can be seen that the sections of the reservoir 3 deviate downwards, which may occur, for example, owing to a fold in the rock formation. The two sections are shown adjoining each other but may also be separated by a layer of rock that does not contain any oil. Two fluid injection wells 10 (well 10d and well 10e) are provided in the reservoir 3 as shown. The two sections 3x, 3y of the reservoir 3 may comprise different rock formation chemical characteristics, oil chemical characteristics and/or formation water chemical characteristics and may also have different initial oil saturations; at least one of these types of characteristics varies such that when measurement data relating to these parameters are input into the predictive model 211 together with measurement data relating to measured chemical characteristics of a proposed displacement fluid, differing predicted data are generated for each section 3x, 3y of the reservoir 3; that is, the predicted amount of incremental oil that will be displaced and potentially recovered, by configuring the crude oil displacement system so as to inject the displacement fluid, differs for each section. It will be appreciated that any number of sections having varying measured chemical characteristics and any number of injection wells 10 can be considered.

Figure 5B:
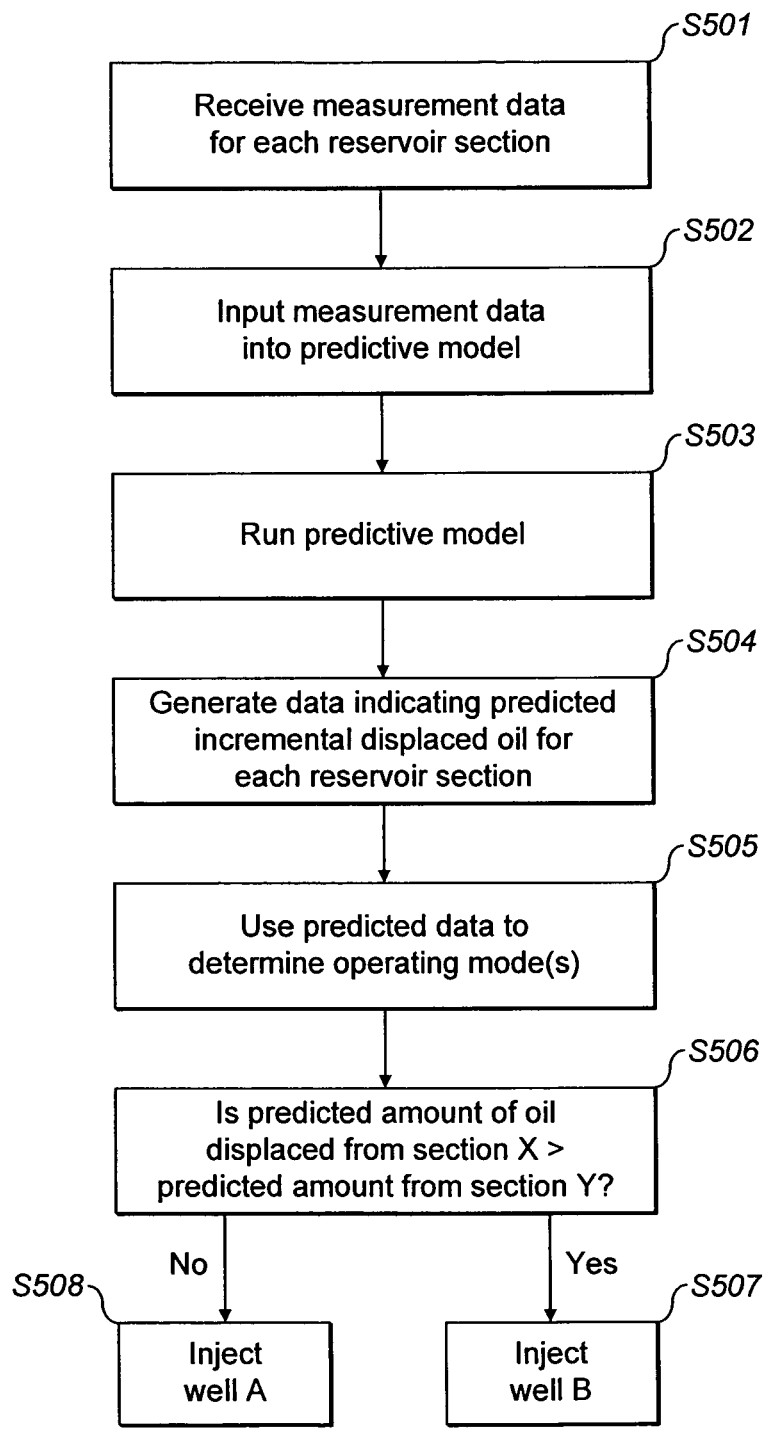

Referring to FIG. 5b, steps S501 to S504 correspond generally to those of the methods of FIGS. 3 and 4b, with measurement data associated with measured chemical characteristics being received for each of the reservoir sections in step S501, and data indicating a predicted amount of displaced oil being generated for each reservoir section in step S504.

In step S505, one or more operating modes of the displacement system are determined based on the predicted data. For example, if it is determined at step S506 that the predicted incremental oil displaced from section 3x, based on the measurement data therefrom, will be greater than that predicted to be displaced from section 3y, the system may determine (step S507) that well 10e is to be injected with the displacement fluid before, or instead of, well 10d. This is because, owing to the positioning of the well and the sections that they are in contact with, a greater proportion of this "higher yielding" section will be flooded, and hence a greater amount of oil will be displaced, by flooding well 10e. The availability of the proposed displacement fluid may be taken into account in such a determination as well as differences in the initial oil saturations for the sections. By contrast, if it is determined at step S506 that the predicted incremental oil displaced from section 3y, based on the measurement data therefrom, will be greater than that predicted to be displaced from section 3x, the system may determine (step S508) that well 10d is to be injected with the displacement fluid before, or instead of, well 10e.

The computer-implemented method and system as applied in the example of FIG. 5a is particularly advantageous where, for example, a low salinity water for use as displacement fluid is in limited supply, and the predictive model 211 can be employed as described above to order or rank the wells in priority order. The predictive model 211 or other system software 213 used in determining the operating mode can use predetermined rules to take into account factors such as the available volume of displacement fluid and the slug volume required to displace this incremental oil for each section of the reservoir in which the oil and/or formation water chemical characteristics measured vary.

Although FIG. 5a shows overlying sections of reservoir that have different chemical characteristics, as discussed above, the chemical characteristics may vary across a reservoir section. Accordingly, the predictive model can be used to rank injection wells that are arranged at different locations in the reservoir and that penetrate the section of reservoir. The predictive model 211 may therefore determine an operating mode where the low salinity water is used as displacement fluid for one or more but not all of the injections wells that penetrate the section of reservoir.

Figure 6:
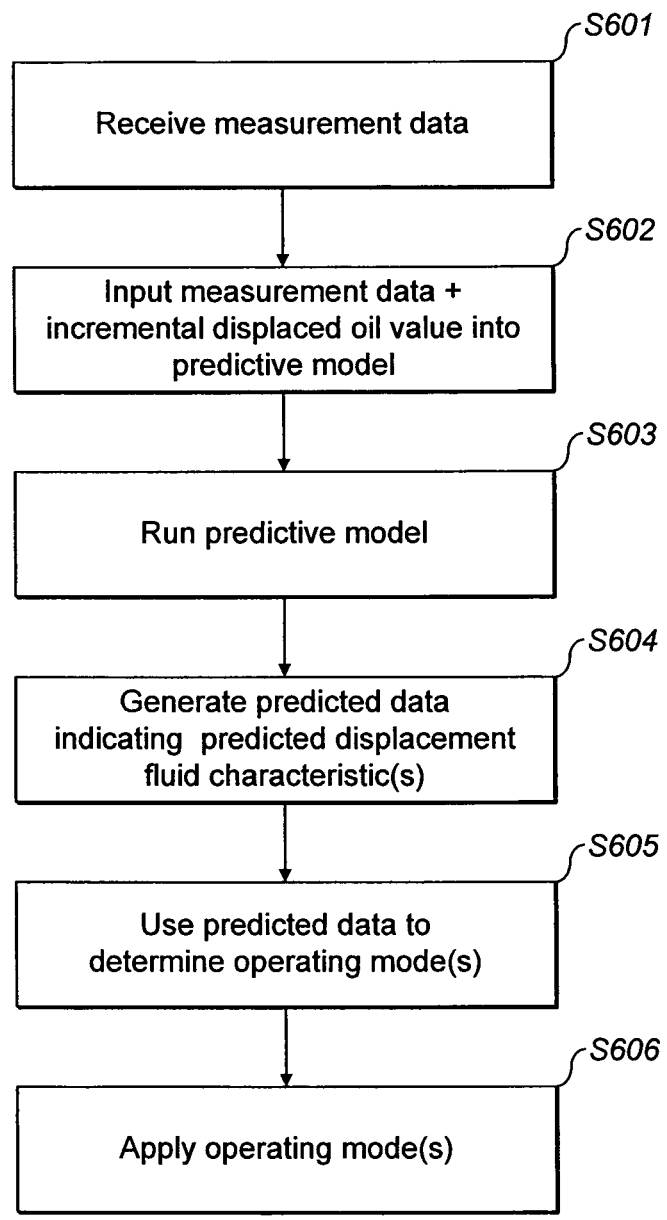
FIG. 6 shows the steps carried out in a method for determining one or more operating modes for a crude oil displacement system, according to a second embodiment of the invention.

Further embodiments of the invention are envisaged. The steps involved in a second embodiment of the computer-implemented method for determining one or more operating modes for the crude oil displacement system are shown in FIG. 6. Steps S601 to S605 are generally similar to steps S301 to S305 of FIG. 3. However, instead of inputting measurement data relating to any chemical characteristics of the displacement fluid, a predetermined threshold value of a required amount of incremental displaced oil, compared with the predetermined volume of oil, is input (step S602) into the computer-implemented predictive model 211, together with the measurement data received from measuring one or more chemical characteristics of the rock formation, and one or more chemical characteristics of the crude oil and the formation water, and upon running the model (step S603) predicted data indicative of one or more predicted chemical characteristics of the displacement fluid is generated (step S604). For example, the generated predicted data can relate to a total dissolved solids (TDS) content and/or multivalent cation content of the displacement fluid necessary to displace at least the predetermined threshold value of incremental displaced oil that was input into the predictive model 211. Thus the chemical characteristics of the aqueous displacement fluid that is required to displace a required amount of incremental oil can be predicted.

At step S605, the predicted data is used to determine one or more operating modes of the crude oil displacement system based on the generated predicted data. The operating mode can represent an instruction or suggested setting for the displacement system, which can subsequently be applied to the displacement system. For example, the operating mode can be an instruction to go ahead with the injection or not, this determination being based on the technical ease and/or resources required to obtain and inject a displacement fluid having the predicted characteristics. Alternatively or additionally, the operating mode can comprise one or more specific configuration settings for the displacement system. In this respect, desalination means, such as a reverse osmosis plant, can be considered to comprise part of the displacement system, and the operating mode can relate to an instruction to proceed with desalination and/or alter one or more settings for the desalination means in order for displacement fluid processed thereby to have a salinity level and/or multivalent cation level that is equal to, or within an acceptable range of, a salinity level and/or multivalent cation level associated with the predicted characteristics.

Again, the computer-implemented method can further include an optional step, S606, of applying or inputting the operating mode determined into a controller of the displacement system.

The computer implemented method may also include an optional step of controlling a blending operation by which the low salinity water that is either naturally occurring or is produced using desalination equipment is blended with the produced water that is separated from the crude oil at the production facility, thereby facilitating disposal of the produced water, and in order to produce a modified low salinity water that is capable of achieving the desired incremental oil displacement. Thus, the predictive model can determine the maximum amount of produced water that can be blended with the low salinity water and still achieve the desired incremental oil displacement.

According to the embodiment described with respect to FIG. 6, by including a value of a required amount of incremental displacement oil in the input characteristics, chemical characteristics of the displacement fluid to be injected to displace this amount of oil, such as chemical characteristics relating to the salinity of the displacement fluid, can be predicted. Again, the above advantages of acquiring an accurate prediction of this information at an early stage apply.

Chemical characteristics such as the total dissolved solids (TDS), which relates to the salinity of the displacement fluid, and/or the multivalent cation content of the displacement fluid, can be predicted by the predictive model 211, and the use of such generated predicted data can be optimised by using additional optimisation software 225 (as shown in FIG. 2) to determine an optimal operating mode for the desalination equipment which forms part of the crude oil displacement system.

It is known that aqueous displacement fluids having a very low TDS content can result in formation damage, arising, for example, from swelling or mobilisation of smectite clays such that the clays block the pores of the formation; such a feature can limit the optimisation of the salinity of the aqueous displacement fluid and hence such data are preferably incorporated in the measurement data input into the predictive model 211 or in the data input into the optimisation software. For example, the smectite clay composition of the rock formation, together with the formation volume and other related characteristics, can be input into the model. The model can be configured such that, if the smectite concentration is above a certain predetermined value, a higher cut-off threshold value is applied for the TDS of the displacement fluid, for example, a higher cut-off threshold of 8,000 ppmv. Data relating to previous, measured formation damage characteristics can also be input as part of the measurement data input into the predictive model 211.

Referring again to FIGS. 1 and 2 and the corresponding description thereof above, the reservoir model 221 or a reservoir simulation can be used in combination with the predictive model 211 described above to provide additional valuable information. This information can also be used to predict when and where optimal recovery of the oil will take place. Based on such predicted data, optimum locations for injection wells and/or production wells can be predicted, allowing the layout of a reservoir or even an entire oilfield to be planned to allow optimal efficiency in oil recovery. Again, the reservoir model uses a predetermined set of rules in conjunction with the relevant input data to generate the required output data.

Optionally, a predetermined threshold value for incremental oil recovery or a predetermined threshold value for the residual oil saturation (i.e. a maximum acceptable value of residual oil volume after oil displacement) of the reservoir 3 may be input into the processing system 200 when the predictive model 211 is run in conjunction with the reservoir model 221. The reservoir model can then calculate the corresponding threshold amount of oil displaced for use by the predictive model in predicting the chemical characteristics of the displacement fluid as described above.

Whilst the embodiments described above involve generating predicted data indicative of an additional amount of oil compared with a predetermined volume of oil, such as a percentage increase in the displaced oil above the predetermined volume, it should be understood that the predictive model can be modified to output an absolute amount of oil displaced by configuring the displacement system so as to inject the displacement fluid in question, thereby avoiding the requirement to input data representing a predetermined volume of oil into the predictive model. Similarly, in relation to the second embodiment, the measurement data can be input together with a predetermined threshold value of a required absolute amount of displaced oil, in order to predict the displacement fluid chemical characteristics. For each embodiment, a comparative step can be performed separately by the system software, if required.

It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

The invention claimed is:

1. A computer-implemented method for determining one or more operating modes for a crude oil displacement system, the crude oil displacement system being arranged to inject an aqueous displacement fluid into one or more reservoirs, each reservoir comprising a porous and permeable rock formation, wherein crude oil and formation water are contained within a pore space of the rock formation, said crude oil displacement system being for use in displacing crude oil from the pore space of the rock formation, the method comprising configuring at least one processor and at least one memory including computer program code to perform the steps of:
receiving measurement data associated with one or more chemical characteristics of the displacement fluid and one or more chemical characteristics of the rock formation, the crude oil and the formation water of the one or more reservoirs;

inputting said measurement data and data representing a predetermined volume of oil into a computer-implemented predictive model stored on the at least one memory;

executing the predictive model so as to generate predicted data indicative of a predicted additional amount of oil, compared with the predetermined volume of oil, that will be displaced from the pore space of the one or more rock formations by injecting said displacement fluid, wherein said predictive data is generated based on said chemical characteristics; and determining, on the basis of the predicted data, said one or more operating modes of the crude oil displacement system;

wherein, if it is determined based on the predicted data that the predicted additional amount of oil that will be displaced from a first section of a said reservoir will be greater than that predicted to be displaced from a second section of the reservoir, the first section is injected with displacement fluid before, or instead, of said second section, and wherein, if it is determined based on the predicted data that the predicted additional amount of oil that will be displaced from a second section of a said reservoir will be greater than that predicted to be displaced from a first section of said reservoir, the second section is injected with displacement fluid before, or instead of, said first section.

2. A method according to claim 1, wherein the step of determining the one or more operating modes includes comparing the predicted data and a predetermined threshold value of oil.

3. A method according to claim 1, wherein the operating modes comprise an instruction to inject the displacement fluid into one or more of the reservoirs.

4. A method according to claim 1, wherein the crude oil displacement system is arranged to inject a displacement fluid into a plurality of reservoirs, the method further including the at least one processor and at least one memory including computer program code to perform the steps of:
    ordering the predicted data associated with the reservoirs based on the predicted amount of displaced oil; and
    determining said one or more operating modes based on the ordered results.

5. A method according to claim 1, wherein the chemical characteristics of the displacement fluid include one or more of the concentration of multivalent cation components and the total dissolved solids (TDS) of the displacement fluid.

6. A method according to claim 1, wherein the chemical characteristics of the rock formation include one or more of the mineral content and the clay content of the rock formation.

7. A method according to claim 1, wherein the chemical characteristics of the crude oil include one or more of the API gravity, the total acid number (TAN) value and the asphaltene and resin components of the oil.

8. A method according to claim 1, wherein the chemical characteristics of the formation fluid include the concentration of multivalent cation components.

9. A computer-implemented method for determining one or more operating modes for a crude oil displacement system, the crude oil displacement system being arranged to inject an aqueous displacement fluid into one or more reservoirs, each reservoir comprising a porous and permeable rock formation, wherein crude oil and formation water are contained within a pore space of the rock formation, said crude oil displacement system being for use in displacing crude oil from the pore space of the rock formation, the method comprising configuring at least one processor and at least one memory including computer program code to perform the steps of:

receiving measurement data associated with one or more chemical characteristics of each of the rock formation, the crude oil and the formation water of the one or more reservoirs;

inputting said measurement data, data representing a predetermined volume of oil and data representing a predetermined threshold value of a required additional amount of oil to be displaced from the pore space of the one or more rock formations compared with the predetermined volume of oil, into a computer-implemented predictive model stored on the at least one memory;

executing the predictive model so as to generate predicted data indicative of one or more predicted chemical characteristics of the displacement fluid, wherein said predictive data is generated based on said chemical characteristics; and determining, on the basis of the predicted data, said one or more injection modes of the crude oil displacement system;

wherein, if it is determined based on the predicted data that the predicted additional amount of oil that will be displaced from a first section of a said reservoir will be greater than that predicted to be displaced from a second section of the reservoir, the first section is injected with displacement fluid before, or instead, of said second section, and wherein, if it is determined based on the predicted data that the predicted additional amount of oil that will be displaced from a second section of a said reservoir will be greater than that predicted to be displaced from a first section of said reservoir, the second section is injected with displacement fluid before, or instead of, said first section.

10. A method according to claim 9, wherein the predetermined threshold value of a required amount of displaced oil comprises a percentage of the oil recovered in a previous oil recovery.

11. A non-transitory computer readable medium comprising a set of instructions, which, when executed by a computer, or a suite of computers, cause the computer or suite of computers to perform the steps according to claim 1.

12. Apparatus for configuring a crude oil displacement system, the crude oil displacement system being arranged to inject an aqueous displacement fluid into one or more reservoirs, each reservoir comprising a porous and permeable rock formation, wherein crude oil and formation water are contained within a pore space of the rock formation, said crude oil displacement system being for use in displacing crude oil from the pore space of the rock formation, the apparatus comprising:
    at least one processor;
    and at least one memory including computer program code;
    the at least one memory and the computer program code being configured to, with the at least one processor, cause the apparatus:
    to receive measurement data based on one or more chemical characteristics of the displacement fluid and one or more chemical characteristics of the rock formation, the crude oil and the formation water of the one or more reservoirs;

generate, based on the measurement data and data representing a predetermined volume of oil, predicted data indicative of a predicted additional amount of oil, compared with the predetermined volume of oil, that will be displaced from the pore space of the one or more rock formations by injecting said displacement fluid having said measured chemical characteristics into the one or more reservoirs; and determine, on the basis of the predicted data, one or more operating modes of the crude oil displacement system;

wherein, if it is determined based on the predicted data that the predicted additional amount of oil that will be displaced from a first section of a said reservoir will be greater than that predicted to be displaced from a second section of the reservoir, the at least one memory and the computer program code is configured to, with the at least one processor, cause said first section to be injected with displacement fluid before, or instead, of said second section, and wherein, if it is determined based on the predicted data that the predicted additional amount of oil that will be displaced from a second section of a said reservoir will be greater than that predicted to be displaced from a first section of the reservoir, the at least one memory and the computer program code is configured to, with the at least one processor, cause said second section to be injected with displacement fluid before, or instead, of said first section.

13. Apparatus according to claim 12, the apparatus being operatively connected to a controller of the crude oil displacement system such that the controller of the displacement system is automatically configured with the one or more operating modes determined by the apparatus, the controller being arranged to apply the one or more operating modes.

14. Apparatus for configuring a crude oil displacement system, the crude oil displacement system being arranged to inject an aqueous displacement fluid into one or more reservoirs, each reservoir comprising a porous and permeable rock formation, wherein crude oil and formation water are contained within a pore space of the rock formation, said crude oil displacement system being for use in displacing crude oil from the pore space of the rock formation, the apparatus comprising:

at least one processor;

and at least one memory including computer program code;

the at least one memory and the computer program code being configured to, with the at least one processor, cause the apparatus:

to receive measurement data based on one or more chemical characteristics of each of the rock formation, the crude oil and the formation water of the one or more reservoirs;

generate, based on (i) the measurement data, (ii) data representing a predetermined volume of oil and (iii) data representing a predetermined threshold value of a required additional amount of oil to be displaced from the pore space of the one or more rock formations compared with the predetermined volume of oil, predicted data indicative of one or more predicted chemical characteristics of the displacement fluid; and determine, on the basis of the predicted data, one or more operating modes of the crude oil displacement system;

wherein, if it is determined based on the predicted data that the predicted additional amount of oil that will be displaced from a first section of a said reservoir will be greater than that predicted to be displaced from a second section of the reservoir, the at least one memory and the computer program code is configured to, with the at least one processor, cause said first section to be injected with displacement fluid before, or instead, of said second section, and wherein, if it is determined based on the predicted data that the predicted additional amount of oil that will be displaced from a second section of a said reservoir will be greater than that predicted to be displaced from a first section of the reservoir, the at least one memory and the computer program code is configured to, with the at least one processor, cause said second section to be injected with displacement fluid before, or instead, of said first section.

15. Apparatus according to claim 14, the apparatus being operatively connected to a controller of the crude oil displacement system such that the controller of the displacement system is automatically configured with the one or more operating modes determined by the apparatus, the controller being arranged to apply the one or more operating modes.

* * * * *